United States Patent [19]

Baldwin et al.

[11] Patent Number: 5,045,561

[45] Date of Patent: Sep. 3, 1991

[54] SUBSTITUTED FURAN SULFONAMIDES AS ANTIGLAUCOMA AGENTS

[75] Inventors: John J. Baldwin, Gwynedd Valley; Gerald S. Ponticello, Lansdale; Harold G. Selnick, Ambler, all of Pa.

[73] Assignee: Merck & Co., Inc., Rahway, N.J.

[21] Appl. No.: 507,806

[22] Filed: Apr. 12, 1990

[51] Int. Cl.$^5$ .................. A61K 31/38; C07D 327/02
[52] U.S. Cl. ............................. 514/432; 514/913; 549/23
[58] Field of Search .............. 549/23; 514/432, 913

[56] References Cited

U.S. PATENT DOCUMENTS

| | | | |
|---|---|---|---|
| 4,677,115 | 6/1987 | Baldwin et al. | 514/432 |
| 4,797,413 | 1/1989 | Baldwin et al. | 514/432 |
| 4,820,848 | 4/1989 | Ponticello et al. | 549/23 |
| 4,824,968 | 4/1989 | Ponticello et al. | 549/23 |
| 4,863,922 | 9/1989 | Baldwin et al. | 514/232.5 |

*Primary Examiner*—Catherine S. Kilby Scalzo
*Attorney, Agent, or Firm*—William H. Nicholson; Joseph F. DiPrima

[57] ABSTRACT

Furan sulfonamides with a saturated heterocycle fused thereto are carbonic anhydrase inhibitors useful in the treatment of elevated intraocular pressure.

7 Claims, No Drawings

SUBSTITUTED FURAN SULFONAMIDES AS ANTIGLAUCOMA AGENTS

SUMMARY OF THE INVENTION

This invention relates to novel aromatic sulfonamides useful in the treatment of elevated intraocular pressure. More particularly this invention relates to compounds having the structural formula:

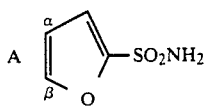

wherein A is as hereinafter defined, as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs currently used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

DETAILED DESCRIPTION OF THE INVENTION

The novel compound of this invention is represented by:

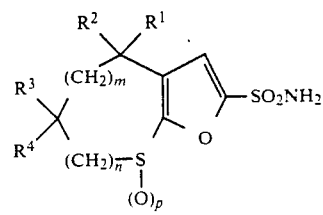

the individual diastereomers, the individual enantiomers or mixtures thereof, or an opthalmologically acceptable salt thereof, wherein:

$R^1$ is
1) hydrogen,
2) hydroxy,
3) $-NR^5R^6$, wherein $R^5$ and $R^6$ independently are:
  a) hydrogen,
  b) $C_{1-6}$alkyl, or
  c) hydroxy-$C_{1-6}$alkyl;

$R^2$ is hydrogen; or
$R^1$ and $R^2$ taken together represent =O;

$R^3$ is
1) hydrogen,
2) $C_{1-6}$alkyl, each either unsubstituted or substituted with
  a) hydroxy,
  b) $C_{1-3}$alkoxy,
  c) $C_{1-3}$alkoxy-$C_{2-3}$alkoxy,
  d) hydroxy-$C_{2-3}$alkoxy, or
  e) $NR^7 R^8$ wherein $R^7$ and $R^8$ independently are:
    i) hydrogen,
    ii) $C_{1-6}$alkyl, or taken together either directly or through a hetero atom selected from O and $-N$ ($C_{1-6}$alkyl) represent a 5-7 membered heterocycle with the nitrogen atom to which they are attached such as pyrrolidine, piperidine, hexahydroazepine; morpholine or N-($C_{1-6}$alkyl) piperazine,
3) $C_{2-6}$alkenyl, or
4) $C_{2-6}$alkynyl, $R^4$ is hydrogen or $C_{1-6}$alkyl;

$R^3$ and $R^4$ taken together, either directly or through a nitrogen atom substituted with hydrogen or $C_{1-6}$alkyl, form a 5-7 membered spirocycle with the carbon to which they are attached, such as a cycloheptane, cyclohexane, cycloheptane, pyrrolidine, piperidine, or hexahydroazepine;

m and n are independently 0, 1 or 2 with the proviso that m+n is not greater than 2; and p is 0, 1 or 2.

It is preferred that $R^1$ is $-NR^5R^6$ wherein $R^5$ is hydrogen and $R^6$ is $C_{1-6}$alkyl. It is also preferred that p is 2.

The term "alkyl", if the number of carbons is unspecified, means $C_{1-6}$alkyl and "alkyl" of three or more carbon atoms includes straight chain, branched chain and cycloalkyl.

Also included within the scope of the present invention are the non-toxic pharmaceutically acceptable salts of the novel compounds. Acid addition salts are formed by mixing a solution of those members of Compound I having a basic nitrogen atom with a solution of a pharmaceutically acceptable non-toxic acid such as hydrochloric acid, fumaric acid, isethionic acid, lactic acid, maleic acid, succinic acid, acetic acid, citric acid, tartaric acid, phosphoric acid, or the like.

Also included within the scope of this invention are diastereomers and enantiomers of the novel compounds and mixtures thereof.

The novel compounds are prepared by the process illustrated in Reaction Scheme I, below.

In this process, a substituted-ω-bromo-($C_{2-4}$alkanoate) derivative 1 is treated with a 2-mercapto-oxazole of the type 2 in a solvent such as ether, THF, $CH_3OH$, $H_2O$, $C_2H_5OH$, DMF or mixtures thereof at about $-20°$ C. to the reflux temperature of the solvent to yield a ω-(2-mercapto-oxazolyl)substituted ($C_{2-4}$alkanoate), 3. In turn, the ester is hydrolyzed to the acid under acid conditions such as aqueous HCl, $CH_3COOH$, aqueous $H_2SO_4$ and aqueous $H_3PO_4$, or basic conditions such as NaOH, KOH, LiOH in solvents such as $H_2O$, alcohol, DMF, THF in a temperature range of $0°$ C. to the reflux temperature of the solvent.

The resulting acid 4 is then transformed to the N,O-dimethylhydroxamide by treating the acid with a carboxyl group activating reagent such as carbonyldiimidazole followed by treatment with an N,O-dialkylhydroxylamine such as dimethylhydroxylamine in solvents such as DMF, THF, methylene chloride, or ether.

The hydroxamides 5 are then transformed into the cyclized products 6 by the following 3-step sequence. Reaction of the N,O-dimethylhydroxamides with the Li salt of acetylene or trimethylsilyl acetylene gives rise to acetylenic ketones which are desilylated by treatment with alkanols such as methanol and then cyclized by heating in a solvent such as benzene, toluene, ethylbenzene, xylenes, or mesitylene from $50°$ C. to the reflux temperature of the solvent.

An alternate synthesis of compound 6 is represented by:

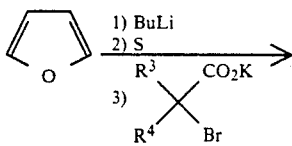

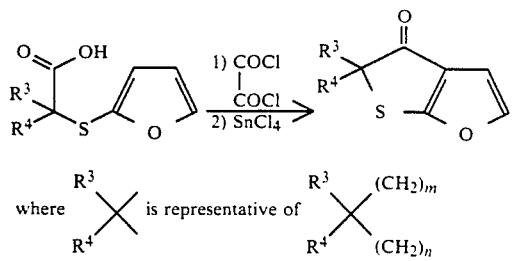

In this procedure, furan in an ethereal solvent such as THF at about $-10°$ to $+10°$ C. is treated with butyl lithium for about 0.5 to 2 hours, then elemental sulfur at about $-10°$ to $+10°$ C. for about 2-3 hours. After diluting with water and extraction with ethyl acetate, the aqueous phase is treated at about $-10°$ to $+10°$ C. with potassium 2-$R^3$-2-$R^4$-3-bromopropionate where m=0 and n=1 and the mixture allowed to warm to room temperature over about 16 to 48 hours. The isolated furyl-3-thiopropionic acid in THF at about $-10°$ to $+10°$ C. is treated with oxalyl chloride and DMF over 2 to 3 hours. After cooling to about dry-ice acetone temperature, $SnCl_4$ is added and the temperature raised to about $0°$ C. slowly.

The compounds 6 are sulfonylated by treatment with sulfuric acid and acetic anhydride in a solvent such as $CH_2Cl_2$ at temperatures ranging from $-20°$ C. to ambient followed by treatment of the sulfonic acids with halogenating reagents such as $PCl_5$ to form the sulfonyl chlorides which are reacted with $NH_4OH$ in acetone or ethyl acetate to form the sulfonamides 7.

The reduction of the carbonyl group can be achieved by standard hydride reduction methods and is best effected by the reaction of $NaBH_4$ in an alcoholic solvent at temperatures ranging from $0°$ C. to ambient to give the hydroxyl derivatives 8.

Compounds of the types 7 and 8 can be converted to the 4-alkylamino compounds by standard methods.

Preparation of the 6,6-dioxides are carried out by treating an alcoholic solution of the thio-compounds with an oxidizing agent such as aqueous OXONE ®.

Alternatively, compounds of types 7 and 8 can be converted to the S,S-dioxides first by treatment with Oxone ® and then converted into the 4-alkylamino compounds.

Reaction Scheme I, for ease of representation is limited to the simplest starting material, 1. It is understood that in each structure of the reaction Scheme, the moiety designated as

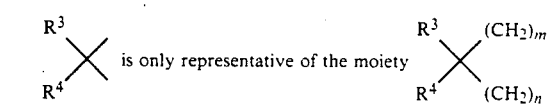

REACTION SCHEME I

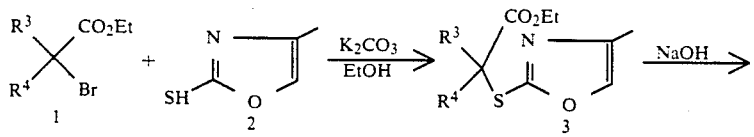

-continued
REACTION SCHEME I

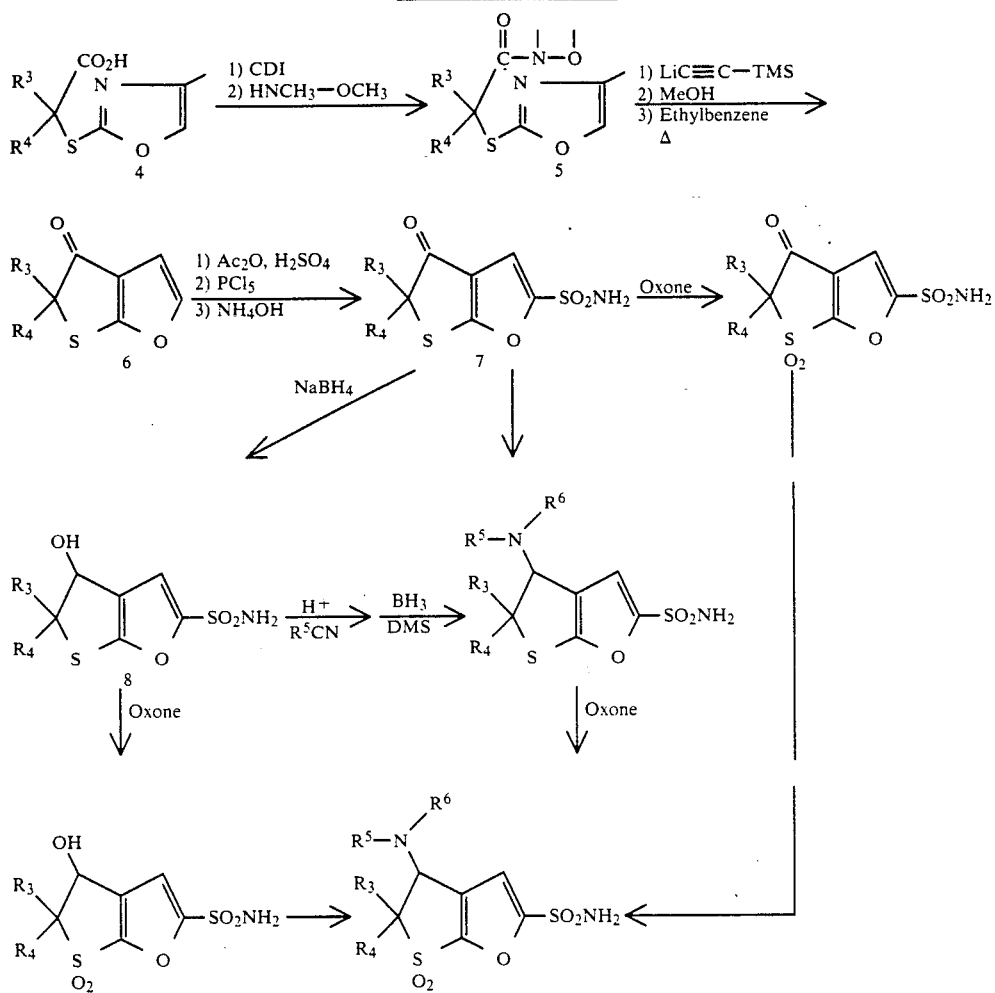

The novel pharmaceutical formulations of this invention are adapted for oral administration such as tablets, capsules or the like; for nasal administration, especially in the form of a spray' for injection, in the form of a sterile injectable liquid; or for topical ocular administration in the form of solutions, ointments, solid water soluble polymeric inserts, or gels.

This invention is particularly concerned with formulations adapted for topical ocular administration for the treatment of glaucoma and other stages of elevated intraocular pressure and contain about 0.1% to 15% by weight of medicament, especially about 0.5 to 4% by weight of medicament, the remainder being comprised of carriers and other excepients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

5,5-dimethyl-4,5-dihydro-4-oxofurano[2,3-b]thiophene-2-sulfonamide.

Step A: Preparation of Ethyl-2-(2-mercapto-4-methyloxazolyl)isobutyrate.

A solution of 30 g (0.26 mole) of 2-mercapto-4-methyloxazole and 50.8 g (0.26 mole) of ethyl-2-bromo-isobutyrate in 300 mL ethanol was treated with 18 g (0.13 mole) of $K_2CO_3$ and heated to reflux for two hours. The reaction was then cooled and stirred at RT for 15 hours. The mixture was then poured into 1L $H_2O$ and extracted with 3×200 mL ether. The combined ether layers were washed with brine, dried over anhydrous $MgSO_4$ and concentrated at reduced pressure to give 50.84 g (85%) of II as a viscous oil. $^1H$ NMR $CDCl_3$ δ7.45 (q, J=1.2 Hz, 1H), 4.17 (q, J=7.1 Hz, 2H), 2.16 (d, J=1.2 Hz, 3H), 1.63 (s, 6H), 1.23 (t, J=7.1 Hz, 3H).

Following the procedure substantially as described in Example 1, Step A, but substituting for the ethyl 2-bromo-isobutyrate used therein the appropriate bromo-esters or bromo acids there were produced the following compounds:

3-(2-mercapto-4-methyloxazolyl)pivalic acid (69% yield) $^1$HNMR CDCl$_3$ δ 10.4–9.4 (brs, 1H) 7.49 (brs 1H) 3.61 (S,2H) 2.27 (q,J=1.3 Hz, 3H) 1.47 (S,6H). HRMS, calculated for C$_9$H$_{13}$NO$_3$S: 215.06167. Found: 215.06161.

Ethyl-4-(2-methyloxazolyl)butyrate (87% yield) $^1$HNMR CDCl$_3$ δ7.36 (brs,1H) 4.13 (q,J=7.1 Hz,2H) 3.19 (t,J=7 Hz,2H) 2.46 (t,J=7.3 Hz,2H) 2.13 (d,J=1.2 Hz,3H) 2.076 (t,J=7.3 Hz,2H) 1.25 (t,J=7.1 Hz,3H)

Methyl-3-methyl-4-(2-mercapto-4-methyloxazolyl) butyrate (69% yield) $^1$HNMR CDCl$_3$ δ7.36 (brs,1H) 3.69 (S,3H) 13.17 (d,J=6.9 Hz,2H) 2.6–2.2 (m,3H) 2.14 (d,J=1.2 Hz,3H) 1.10 (d,J=7 Hz,3H). Mass spec. M+ peak=229.

Step B: Preparation of 2-(2-mercapto-4-methyloxazolyl)isobutyric acid

A 1L rb flask was charged with 50 g of product from Step A (0.218 mole) and 500 mL of 1N NaOH. The mixture was stirred vigourously for four hours until all of the starting material had dissolved. The reaction was diluted with 1L H$_2$O and extracted with 100 mL ether. The aqueous phase was then acidified to pH 2 and extracted repeatedly with ether. The ether layers were combined, dried over MgSO$_4$ and concentrated in vacuo to give 41.3 g (94%) of acid II; MP=93° C.; $^1$H NMR CDCl$_3$ δ 7.46 (brs, 1H), 2.2 (brs, 3H), 1.67 (s, 6H). High resolution mass spectrum calcd. for C$_8$H$_{11}$NO$_3$S: 201.0459. Found: 201.0464.

Following the procedure substantially as described in Example 1, Step B, but substituting for the ethyl 2-(2-mercapto-4-methyloxazolyl) isobutyrate the other 4-methyloxazoles described in Example 1, Step A there were produced the following:

4-(2-mercapto-4-methyloxazolyl) butyric acid (90% yield) $^1$HNMR CDCl$_3$ δ 7.37 (brs,1H) 3.22 (q,J=1.6 Hz,2H) 2.57 (d,J=6 Hz,2H) 2.18 (S,3H) 2.1 (d,J=6 Hz,2H).

3-methyl-4-(2-mercapto-4-methyloxazolyl) butyric acid (100% yield) $^1$HNMR CDCl$_3$ δ 8.5–7.5 (brs,1H) 7.36 (q,J=1.2 Hz,1H) 3.2 (d,J=5.5 Hz,2H) 2.6–2.3 (m,3H) 2.14 (d,J=1.2 Hz,3H) 1.12 (d,J=6.6 Hz,3H). Mass spec. M+ peak=215.

Step C: Preparation of 2-(2-mercapto-4-methyloxazolyl)-N,O-dimethyl isobutyryl hydroxamide A solution of 10 g (49.7 mmole) of the carboxylic acid from Step B in 30 mL DMF at 0° C. was treated with 9.66 g (59.6 mmole) of carbonyl diimidazole in small portions. Into another flask, a solution of 8.72 g (89.44 mmole) of O,N-dimethylhydroxylamine.HCl and 60 mL DMF was treated with 9.85 g (99.38 mmole) of N-methylpiperidine and the precipitate was filtered off. The remaining two solutions were then combined at 0°. The reaction was warmed to RT and stirred for 5 hours. The reaction mixture was then poured into 700 mL ice cold H$_2$O and the product isolated by extracting with 3x 200 mL portions of ether. The combined ether layers were washed once with 50 mL ice cold 0.2N HCl and 50 mL brine, in that order. The ether solution was then dried over MgSO$_4$ and concentrated in vacuo. The residue was chromatographed on silica gel using 1:1 ethyl acetate/hexanes as eluent to give 6.9 g (57%) of amide II as a viscous oil. $^1$H NMR CDCl$_3$ δ7.45 (brs, 1H), 3.80 (s, 3H), 3.26 (s, 3H), 2.16 (brs, 3H), 1.63 (s, 6H). High resolution mass spectrum calcd. for C$_{10}$H$_{16}$N$_2$O$_3$S: 244.0881. Found: 244.0872.

Employing the procedure substantially as described in Example 1, Step C, but substituting for the 2-(2-mercapto-4-methyloxazolyl)-isobutyric acid used therein the other carboxylic acids described in Steps A and B, there were produced the following:

2,2-Dimethyl-3-(2-mercapto-4-methyloxazolyl) N,O-dimethyl butyryl hydroxamide (74% yield) $^1$HMNR CDCl$_3$ δ7.33 (q,J=12 Hz,1H) 3.69 (S,3H) 3.5 (S,2H) 3.19 (S,3H) 2.13 (d,J=1.2 Hz,3H) 1.38 (S,6H) HRMS calc'd for C$_{11}$H$_{18}$N$_2$O$_3$S: Requires: 258.1038. Found: 258.1032.

3-(2-mercapto-4-methyloxazolyl)N,O-dimethyl butyryl hydroxamide (74% yield) $^1$HNMR CDCl$_3$ δ 7.36 (q,J=12 Hz,1H) 3.68 (S,3H) 3.22 (t,J=7 Hz,2H) 317 (s,3H) 2.6 (t,J=7.2 Hz) 2.13 (d,J=1.2 Hz,3H) 2.08 (m,2H).

3-methyl-4(2-mercapto-4-methyloxazolyl) N,O-dimethyl butyrylhydroxamide (75% yield) $^1$HNMR CDCl$_3$ δ 7.35 (q,J=1.2 Hz,1H) 3.66 (S,3H) 3.2 (d,J=6.3 Hz,2H) 3.17 (S,3H) 2.7–2.2 (m,3H) 2.13 (d,J=1.2 Hz,3H) 1.1 (d,J=6.5 Hz,3H). Mass spec. M+ peak=258.

Step D: Preparation of 5,5-dimethyl-4,5-dihydro-4-oxofurano[2,3-]thiophene

A solution of 4.82 g (49.11 mmole) of trimethylsilyl acetylene in 150 mL THF at 0° C. was treated with 49.1 mL of a 1M solution of lithium bis trimethylsilyl amide. The solution was allowed to stir at 0° C. for five minutes and then a solution of 10 g (40.93 mmoles) of 2-(2-mercapto-4-methyloxazolyl)-2-methyl-N,O-dimethylpropionyl hydroxamide in 20 mL THF was added and the reaction warmed to RT. After stirring at RT for a ½ hour, the solution was poured into 500 mL H$_2$O and extracted with ether. The combined ether layers were washed with brine, dried over MgSO$_4$ and concentrated in vacuo. The crude material was then dissolved in ≃200 mL MeOH and concentrated in vacuo to effect desilylation. The crude material was then dissolved in 400 mL of ethyl benzene and heated at reflux in an inert atmosphere for one hour. The reaction was cooled to RT, concentrated in vacuo and chromatographed on silica gel using 3:2 hexane/methylene chloride to give 4.33 g (63%) of 5,5-dimethyl-4-oxo-4,5-dihydro-furano [2,3-b]thiophene as a viscous oil. $^1$HNMR CDCl$_3$ δ 7.53 (d, J=2.1 Hz, 1H), 6.64 (d, J=2.1 Hz, 1H), 1.68 (s, 6H). HRMS calc'd for C$_8$H$_8$O$_2$S: 168.0221. Found: 168.0229.

Employing the procedure substantially as described in Example 1, Step D, but substituting for the 2-(2-mercapto-4-methyloxazolyl)-2-methyl-N,O-dimethylpropionyl hydroxamide used therein, the other hydroxamides described in Step C, there were produced the following:

5,5-dimethyl-5,6-dihydro-4-oxofurano[2,3-b]thiopyran (91% yield) $^1$HNMR CDCl$_3$ δ 7.35 (d,J-2.1 Hz,1H) 6.78 (d,J=2.1 Hz,1H) 3.17 (S,2H) 1.30 (S,6H). HRMS calculated for C$_9$H$_{10}$O$_2$S: 182.0401. Found: 182.0399.

4,5,6,7-tetrahydro-4-oxofurano[2,3-b]thiepin (68% yield) $^1$HNMR CDCl$_3$ δ 7.38 (d,J=2 Hz,1H) 6.8 (d,J=2H,1H) 3.08 (t,J=6 Hz,2H) 2.95 (t,J=6 Hz,2H) 2.28 (p,J=6 Hz,2H). Mass spec. m/e=168 (M+).

4,5,6,7-tetrahydro-6-methyl-4-oxofurano[2,3-b]thiepin (63% yield) $^1$HNMR d$_6$DMSO δ 8.20 (d,J=2 Hz,1H) 7.21 (d,J=2 Hz,1H) 3.69 (dd,J=5.3,14.2 Hz,1H) 3.40-3.25(m,2H)3.1-3 (m,2H) 1.51 (d,J=6.1 Hz,3H). Mass spec. m/e (76)=182(100,M+) 167(M+-15,41).

Step E: Preparation of 5,5-dimethyl-4,5-dihydro-4-oxofurano[2,3-b]thiophene-2-sulfonamide A solution of 1 g (5.94 mmole) of the ketone in 10 mL methylene chloride at 0° C. was treated with 606 mg (5.94 mmole) of acetic anhydride followed by 583 mg (5.94 mmole) of sulfuric acid. The reaction was warmed slowly to RT over one hour. Hexane (≃5 mL) was added to induce crystallization and the supernatant decanted. Methylene chloride was added and the suspension was cooled to 0° C. and treated with 1.85 g (8.91 mmole) phosphorous pentachloride. The reaction was stirred at 0° C. for 1½ hours and then warmed to RT for ½ hours. The dark purple reaction mixture was then poured into ice water and extracted with ethyl acetate. The combined organic layers were washed once with brine, dried over magnesium sulfate and concentrated at reduced pressure. The crude sulfonyl chloride was dissolved in 50 mL of acetone and treated with excess concentrated ammonium hydroxide. The mixture was then concentrated to remove the acetone and residue partitioned between ethyl acetate and water. The combined organics were washed with brine, dried over magnesium sulfate and concentrated in vacuo. Chromatography on silica gel using 40% ethyl acetate/hexanes as eluent gave, after crystallization from ethyl acetate/hexane, 542 mg (37%) of 5,5-dimethyl-4,5-dihydro-4-oxo-furano [2,3-b]thiophene-2-sulfonamide. MP=167°-9°. High resolution mass spectrum calcd. for C$_8$H$_9$NO$_4$S$_2$: 248.0037. Found: 248.0051.

Combustion analysis calcd. for C$_8$H$_9$NO$_4$S$_2$: C, 38.85; H, 3.66; N, 5.66. Found: C, 38.92; H, 3.79; N, 5.69.

Employing the procedure substantially as described in Example 1, Step E, but substituting for the 5,5-dimethyl-4,5-dihydro-4-oxofurano[2,3-b] thiophene used therein, the other furans described in Step D, there were produced the following:

5,5-dimethyl-5,6-dihydro-4-oxo-4H-furano[2,3-b]thiopyran-2-sulfonamide (31% yield) MP=230° C. $^1$HNMR d$_6$ DMSO δ 7.95 (S,2H) 7.13 (S,1H) 3.48 (S,2H) 1.19 (S,6H) HRMS calculated for C$_9$H$_{11}$NO$_4$S$_2$: 262.0207. Found: 262.0202.

4,5,6,7-Tetrahydrofurano[2,3-b]thiepin-4-oxo-2-sulfonamide (55% yield) MP=188°-191° C. $^1$HNMR d$_6$ DMSO δ 7.90 (S,2H) 7.02 (S,1H) 3.25 (t,J=6.5 HZ,2H) 2.80 (t,J=6.5 Hz,2H) 2.33 (p,J=6.5 Hz,2H).

6-methyl-4,5,6,7-tetrahydrofurano[2,3-b]thiepin-4-oxo-2-sulfonamide (31% yield) MP=153°-4° C. $^1$HNMR d$_6$ DMSO δ 7.92 (S,2H) 7.02 (S,1H) 3.4-3.2 (m,1H) 3.1-2.8 (m,2H) 2.7-2.55 (m,1H) 1.05 (d,J=6.2 Hz,3H)

EXAMPLE 2

5,5-dimethyl-4,5-dihydro-4-hydroxy-4H-furano[2,3-b]thiophene-2-sulfonamide

A solution of 520 mg (2.1 mmole) of 4,5-dihydro-5,5-dimethyl-4-oxofurano[2,3-b]thiophene-2-sulfonamide in 20 mL ethanol at RT was treated with 95 mg (2.5 mmole) of sodium borohydride. The reaction was stirred at RT for one hour and then concentrated to remove the ethanol. The residue was partitioned between ethyl acetate and saturated sodium bicarbonate, and the aqueous phase was extracted with two additional portions of ethyl acetate. The organic layers were dried over magnesium sulfate and concentrated at reduced pressure to give 506 mg (96%) of essentially pure material. Crystallization from acetone/dichloroethane gave 195 mg of material that melted at 147°. $^1$H NMR DMSO-D$_6$ δ 7.67 (s,2H), 6.99 (s,1H), 5.59 (d, J=6.8 Hz, 1H), 4.40 (d, J=6.8 Hz, 1H), 1.56 (s, 3H), 1.52 (s, 3H).

Analysis calcd. for C$_8$H$_{11}$NO$_4$S$_2$: C, 38.54; H, 4.44; N, 5.61 Found: C, 38.30; H, 4.67: N, 5.55.

Employing the procedure substantially as described in Example 2, but substituting for the 5,5-dimethyl-4,5-dihydro-4-oxofurano[2,3-b]thiophene-2-sulfonamide used therein, the other oxo compounds described in Example 1, Step E, there were prepared:

5,6-Dihydro-4-hydroxy-5,5-dimethyl-4H-furano[2,3-b]thiopyran-2-sulfonamide (86% yield) MP=76°-79° C. $^1$HNMR d$_6$ DMSO δ 7.65 (S,2H) 6.93 (S,1H) 5.30 (d,J=5.7 Hz,1H) 4.10-3.99 (m,2H) 3.10 (d,J=126 Hz,1H) 2.87 (d,J=12.6 Hz,1H) 1.026 (S,3H) 0.97 (s,3H). Mass spec (m/e)=263 (M+, 135%).

Analysis calculated for C$_9$H$_{13}$NO$_4$S$_2$. 0.9CHCl$_3$ C,32.13; H,3.77; N,3.78;Cl,25.87. Found: C,32.38; H,3.94; N,3.72; Cl,27.1.

4-hydroxy-4,5,6,7-tetrahydro-4H-furano[2,3-b]thiepin-8,8-dioxide-2-sulfonamide (The starting material was prepared as described in Example 5). (93% yield) MP=192°-195° C. $^1$HNMR d$_6$ DMSO δ 8.1 (S,2H) 7.01 (S,1H) 5.8 (d,J=5.5 Hz,1H) 4.75-4.7 (m,1H) 3,65-3.55 (m,2H) 2.3-1.7 (m,4H).

Analysis calc'd for C$_8$H$_{11}$O$_6$N: C,,34.15; H,3.94; N,4.98. Found: C,33.78; H,3.68; N,4.83.

EXAMPLE 3

5,6-Dihydro-5,5-dimethyl-4-ethylamino-4H-furano[2,3-b]thiopyran-2-sulfonamide

A solution of ethylamine (4.83 g, 107 mmol) and 5,5-dimethyl-5,6-dihydro-4-oxo-4H-furano[2,3-b] thiopyran-2-sulfonanide (2.8 g, 10.7 mmol) in 80 mL 1:1 THF Benzene at 0° C. was treated with 1.01 g (597 μL, 5.35 mmol) TiCl$_4$ via syringe. The reaction was warmed to room temperature and stirred for five hours. The reaction was then filtered and the filtrate comcentrated in vacuo. The residue was dissolved in ethanol (40 mL) and treated with excess NaBH$_4$ at room temperature. After 15 minutes, the reaction was poured into saturated NaHCO$_3$ (300 mL) and extracted with ethyl acetate (3×100 mL). The combined ethyl acetate layers were extracted with 0.2 N HCl. The acidic aqueous phase was basified to pH 9.5 and extracted repeatedly with ethyl acetate. These ethyl acetate extracts were combined, dried over MgSO$_4$, filtered and concentrated in vacuo to give 1.12 g. The crude material was dissolved in ethanol and treated with excess ethanolic HCl. The ethanol was evaporated at reduced pressure and the residue crystallized from isopropanol. MP=147° C. $^1$HNMR d$_6$ DMSO δ 9.05 (brs,1H) 8.5 (brs,1H) 7.8 (S,2H) 7.22 (S,1H) 4.01 (m,1H) 3.79 (d,J=12Hz,1H) 3.13-2.85 (m,3H) 1.33-1.3 (m,6H) 1.00 (S,3H). Mass spec 290 M+.

Anal calc'd for C$_{11}$H$_{18}$N$_2$O$_3$S$_2$.HCl.0.7(CH$_3$)-CHOH: N,7.59; C,42.64; H,6.72. Found: N,7.48; C,42.56; H,7.705.

Following the procedure substantially as described in Example 3, but substituting for the 5,5-dimethyl-5,6-dihydro-4-oxo-4H-furano[2,3b]-thiopyran-2-sulfonamide used therein, the other oxo-compounds described in Example 1, Step E there were produced the following:

5,6-dihydro-4-isobutylamino-5,5-dimethyl-4H-furano-[2,3-b]thiopyran-2-sulfonamide hydrochloride Crystallization solvent was isopropanol (88% yield). The hydrochloride melted at 152° C.

Analysis calculated for C$_{13}$H$_{22}$O$_3$S$_2$.HCl.C$_3$H$_8$O): N,6.75; C,46.30; H,7.52. Found: N,6.82; C,46.11; H,7.42.

5,5-dimethyl-4,5-dihydro-4-ethylamino-furano[2,3-b-]-thiophene-2-sulfonamide hydrochloride Crystallization solvent was isopropanol (40% yield). MP=149°-152° C. for hydrochloride. $^1$HNMR d$_6$ DMSO δ9.48 (brs,1H) 9.22 (S,2H) 7.29 (S,1H) 4.38 (d,J=5 Hz,1H) 3.03-2.85 (m,2H) 1.85 (S,3H) 1.7 (S,3H) 1.3 (t,J=6 HZ,3H).

Analysis calculated for C$_{10}$H$_{15}$N$_2$O$_3$S$_2$.HCl.iPrOH: N,7.51; C,41.86; H,6.75. Found: N,7.50; C,41.57; H,6.57.

EXAMPLE 4

4,5,6,7-tetrahydro-4H-4-ethylamino-6-methylfurano-[2,3-b]thiepin-2-sulfonamide-8,8-dioxide The reductive amination of 6-methyl-4-oxo-4,5,6,7-tetrahydrofurano[2,3-b]thiepin-2-sulfonamide described in Example 3 provided 1.71 g, 90% yield of the thiepin as a mixture of cis and trans isomers. The isomers were not separated at this stage. The crude material (thiepins) was dissolved in MeOH, and OXONE ® (2 eq) in H$_2$O was added and the mixture stirred overnight. The reaction was poured into saturated NaHCO$_3$ solution and extraced with ethyl acetate. The organic layers were combined, dried over MgSO$_4$, filtered and concentrated in vacuo. Chromatography of the residue on silica gel eluting with 8% MeOH/CHCl$_3$ gave 570 mg of β isomer and 550 mg of α isomer. The HCl salts were generated in ethanol. The β isomer melted at 258°-260° C.

Analysis calculated for C$_{11}$H$_{18}$N$_2$O$_5$S$_2$.HCl: N,7.81; C,36.81; H,5.34. Found: N,8.02; C,36.71; H,5.68. The σ isomer melted at 259°-261° C.

Analysis calc'd for C$_{11}$H$_{18}$N$_2$O$_5$S$_2$.HCl: N,7.81; C,36.81; H,5.34. Found: N,7.64; C,36.8; H,5.34.

EXAMPLE 5

5,5-dimethyl-5,6-dihydro-4H-4-hydroxyfurano[2,3-b]-thiopyran-7,7-dioxide-2-sulfonamide A solution of 5,5-dimethyl-5,6-dihydro-4-hydroxy-furano-[2,3-b] thiopyran-2-sulfonamide (1g, 3.79 mmol), in 20 mL methanol was cooled to 0° C. and treated with a solution of 3.49 g (5.69mmol) OXONE ® in water. The reaction mixture was warmed to room temperature and stirred overnight. The reaction was poured into saturated aqueous NaHCO$_3$ solution and extracted repeatedly with ethyl acetate. The combined organic layers were dried over MgSO$_4$, filtered and concentrated in vacuo. Chromatography of the residue on silica gel eluting with 80%-100% ether/hexanes gave 989 mg (88%) of product, which was crystallized from ether/CHCl$_3$. MP=156°-8° C. $^1$HNMR d$_6$ DMSO δ 8.17 (S,2H) 7.09 (brs,2H) 1.13 (S,3H) 1.05 (S,3H).

Analysis calculated for C$_9$H$_{13}$NO$_6$S$_2$: C,36.60; H,4.43; N,4.74. Found: C,36.48; H,4.56; N,4.65.

Employing the procedure substantially as described in Example 5. The following compounds were prepared from the corresponding thio-compounds:

4,5-Dihydro-5,5-dimethyl-4-hydroxy-4H-furano[2,3-b]-thiophene-6,6-dioxide-2-sulfonamide (81% yield). MP=181°-182° C. $^1$HNMR d$_6$ DMSO δ 8.19 (S,2H) 7.22 (S,1H) 4.79 (S,1H) 1.44 (S,3H) 1.35 (S,3H)

| Elemental analysis for C$_8$H$_{11}$NO$_6$S$_2$: | | | |
|---|---|---|---|
| | C | N | H |
| Calculated: | 34.15 | 4.97 | 3.94 |
| Found: | 34.25 | 5.00 | 3.78 |

5,6-Dihydro-5,5-dimethyl-4-ethylamino-4H-furano[2,3b]-thiopyran-2-sulfonamide-7,7-dioxide hydrochloride (40% yield) MP=273°-275° C. $^1$HNMR d$_6$ DMSO δ 9.65 (brs,1H) 9.03 (brs,1H) 8.28(S,2H) 7.47 (S,1H) 4.45-4.3 (m,2H) 3.76(d,J=15Hz,1H) 3.18 (brs,1H) 3.02 (brs,1H) 1.38 (S,3H) 1.32 (t,J=7 Hz,3H) 1.25 (S,3H).

| Elemental analysis for C$_{11}$H$_{18}$N$_2$O$_5$S$_2$—HCl | | | |
|---|---|---|---|
| | C | H | N |
| Calculated: | 36.81 | 5.33 | 7.80 |
| Found: | 36.89 | 5.42 | 7.63 |

4-isobutylamino-5,6-Dihydro-5,5-dimethyl-4H-furano-[2,3-b]thiopyran-2-sulfonamide-7,7-dioxide hydrochloride MP=264° C. $^1$HNMR d$_6$ DMSO δ 9.42 (brs,1H) 8.3(S,2H) 7.52 (S,1H) 4.5-4.3 (m,2H) 3.75 (d,J=15 Hz,1H) 3.6 (m,2H) 3.05-2.85 (m,2H) 2.3-2.1 (m,1H) 1.49 (brs,3H) 1.26 (S,3H) 0.98 (d,J=6.5 HZ,6H)

| Elemental analysis for C$_{13}$H$_{22}$N$_2$O$_5$S$_2$.HCl | | | |
|---|---|---|---|
| | C | H | N |
| Calculated: | 40.35 | 5.99 | 7.24 |
| Found: | 40.27 | 5.77 | 7.13 |

4,5,6,7-tetrahydrofurano[2,3-b]thiepin-4-oxo-8,8-dioxide-2-sulfonamide (80% yield) MP=188°-190° C. $^1$HNMR d$_6$ DSMO δ 8.28 (S,2H) 7.20(S,1H) 4.02 (m,2H) 2.91 (m,2H) 2.3 (m,2H).

| Elemental analysis for C$_8$H$_9$O$_6$N. | | | |
|---|---|---|---|
| | C | H | N |
| Calculated: | 34.40 | 3.25 | 5.02 |
| Found: | 34.73 | 3.21 | 4.92 |

4,5,6,7-tetrahydro-6-methylfurano[2,3-b]thiepin-4-oxo-8,8-dioxide-2-sulfonamide (100% yield) MP=177°-180° C. from ethyl acetate. $^1$HNMR d$_6$ DMSO δ 8.30 (S,2H) 7.21 (S,1H) 4.1-3.8 (m,2H) 3.45-3.3 (m,2H) 2.9 (m,2H) 2.75-2.6 (m,1H) 1.18 (d,J=6Hz,3H).

| Elemental analysis for C$_9$H$_{11}$NO$_6$S$_2$. | | | |
|---|---|---|---|
| | C | H | N |
| Calculated: | 37.10 | 3.81 | 4.81 |
| Found: | 36.99 | 3.79 | 4.70 |

EXAMPLE 6

4,5,6,7-tetrahydro-4-isobutylamino-4H-furano[2,3-b]-thiepin-2-sulfonamide-8,8-dioxide.

A solution of 500 mg (1.8 mmol) of 4,5,6,7-tetrahydrofurano[2,3-b]thiepin-4-oxo-2-sulfonamide in ~20 mL THF was treated with 3 g of 3 Å molecular sieves and 540 mL (395 mg, 5.4 mmol) of isobutylamine and heated to reflux for four hours. The reaction was then cooled to 0° C. and diluted with ~50 mL ethanol. Excess NaBH$_4$ was then added and the reaction stirred at room temperature for two hours. The ethanol was evaporated at reduced pressure and the residue was partitioned between ethyl acetate and saturated aqueous sodium bicarbonate solution. The combined organic extracts were dried over MgSO$_4$, filtered and concentrated in vacuo. The hydrochloride salt was generated in CH$_3$OH/C$_2$H$_5$OH with excess ethanolic HCl. On cooling overnight, a crystalline solid separated which was collected and dried under vacuum for 72 hours. Yield: 287 mg (42%).

MP=261°-263° C., $^1$HNMR (360 MHO) d$_6$ DMSO δ9.75 (s,1H)
9.40 (S,1H) 8.35 (S,2H) 7.49 (S,1H) 4.60 (m,1H) 3.88-3.6 (m,2H) 2.80 (brs,2H) 2.48-2 (m,5H) 1.02 (d,J=6 Hz,6H).

| Elemental analysis for C$_{12}$H$_{20}$N$_2$O$_5$S$_2$.HCl | | | |
|---|---|---|---|
| | C | H | N |
| Calculated: | 38.64 | 5.67 | 7.51 |
| Found: | 38.63 | 5.53 | 7.5 |

The following compounds were prepared in an analogous manner to that described in Example 6.

4,5,6,7-tetrahydrofurano-4H-4(n-propylamino)-[2,3-b]-thiepin-2-sulfonamide-8,8-dioxide hydrochloride 109 mg (33% yield) MP=247°-249° C. from Ethanol/Ether $^1$HNMR d$_6$ DMSO δ 10.05 (brs,1H) 9.55 (brs,1H) 8.25 (S,2H) 7.49(S,1H) 4.65(m,1H) 3.86-3.66(m,2H) 3.06-2.8 (m,2H) 2.4-1.9 (m,4H) 1.75(q,J=6Hz,2H) 0.95 (t,J=6Hz,3H)

| Elemental analysis for C$_{11}$H$_{18}$N$_2$O$_5$S$_2$.HCl.0.5 H$_2$O. | | | |
|---|---|---|---|
| | C | H | N |
| Calculated: | 36.36 | 5.40 | 7.71 |
| Found: | 36.25 | 5.01 | 7.54 |

4,5,6,7-tetrahydro-4H-4-(isobutylamino)-6-methyl-furano[2,3-b]thiepin-2-sulfonamide-8,8-dioxidehydrochloride cis isomer: 221 mg (34% yield) MP=236°-238° C. from Isopropanol.

| Elemental analysis for C$_{13}$H$_{22}$N$_2$O$_5$S$_2$.HCl.C$_3$H$_8$O. | | | |
|---|---|---|---|
| | C | H | N |
| Calculated: | 42.98 | 6.99 | 6.26 |
| Found: | 42.66 | 6.91 | 5.91 | tran isomer: 230 mg (36% yield) MP=205°-208° C. (isopropanol).

| Elemental analysis for C$_{13}$H$_{22}$N$_2$O$_5$S$_2$.HCl.0.25 H$_2$O. | | | |
|---|---|---|---|
| | C | H | N |
| Calculated: | 39.88 | 6.05 | 7.15 |
| Found: | 39.92 | 5.78 | 7.11 |

EXAMPLE 7

5,5-dimethyl-4,5-dihydro-4H-4-ethylaminofurano[2,3-b]thiophene-6,6-dioxide-2-sulfonamide hydrochloride A solution of 296 mg (0.79 mmol) of 5,5-dimethyl-4,5-dihydro-4H-4-ethylaminofurano[2,3-b]thiophene-2-sulfonamide in pyridine at room temperature was treated with 122 mg (1.19 mmol) acetic anhydride, 242 mg (2.4 mmol) triethylamine and 9.7 mg (0.079 mmol) dimethylaminopyridine. The reaction was stirred at room temperature for ½ hour and poured into 30 mL saturated aqueous sodium bicarbonate solution. The aqueous phase was extracted repeatedly with ethyl acetate. The combined organic layers were dried over magnesium sulfate, filtered and concentrated in vacuo. The crude amide was dissolved in 5 mL CH$_3$OH and treated with OXONE® (765 mg, 12.4 mmol) in 5 mL H$_2$O at room temperature for 24 hours. The reaction mixture was poured into 100 mL saturated aqueous NaHCO$_3$ solution and extracted repeatedly with ethyl acetate. The combined organics were dried over anhydrous MgSO$_4$, filtered and concentrated in vacuo. The crude sulfone was dissolved in 5 mL MeOH and treated with 5 mL 6N HCl and heated to reflux overnight. The reaction was cooled to room temperature, diluted with 20 mL of H$_2$O, and extracted with ethyl acetate. The aqueous phase was then basified to pH 9.5 and extracted with ethyl acetate. These ethyl acetate extractions were combined, dried over MgSO$_4$, filtered and concentrated in vacuo. The hydrochloride salt was generated in ethanol with excess ethanolic HCl. The crude HCl salt was crystallized from isopropanol. 48 mg MP= 239° C. $^1$HNMR d$_6$ DMSO δ 10.1 (brs, 1H) 9.65 (brs, 1H) 8.37 (S, 2H) 7.63 (S, 1H) 4.90)m, 1H) 3.6-3 (m, 4H) 1.62 (S, 6H) 1.30 (t, J=6Hz, 3H).

| Elemental analysis for C$_{10}$H$_{16}$N$_2$O$_5$S$_2$.HCl.0.2C$_3$H$_8$O. | | | |
|---|---|---|---|
| | C | H | N |
| Calculated: | 35.67 | 5.25 | 7.80 |
| Found: | 35.50 | 5.12 | 7.88 |

EXAMPLE 8

5,6-Dihydro-4-isobutylamino-4H-furano[2,3-b]thiopyran-2-sulfonamide-7,7-dioxide

Step A: Preparation of 3-(2-furylthio)propionic acid

A solution of 15 g (0.22 mol) of furan in 500 mL THF at 0° C. was treated with 88 mL of 2.5N n-BuLi in hexanes dropwise with stirring. After one hour at 0° C. sulfur (7.07 g, 0.22 mol) was added and the mixture stirred for another 2½ hours at 0° C. The reaction was then poured into 1.5 L $H_2O$ and extracted twice with ethyl acetate. The aqueous phase was then concentrated for ∼15 minutes at reduced pressure to remove excess organics.

In a separate flask 15.3 g (0.22 mol) $K_2CO_3$, 500 mL $H_2O$ and 33.75 g (0.22 mol) 3-bromopropionic acid were combined and stirred until a clear solution was obtained. Both solutions were cooled to 0° and combined and allowed to warm slowly to room temperature. The reaction was kept at room temperature for 24 hours, and poured into $H_2O$. The pH was adjusted to ∼2-3 and the aqueous phase was extracted repeatedly, with ethyl acetate. The organics were dried over $MgSO_4$, filtered and concentrated in vacuo. The residue was distilled in a Kugelrohr apparatus to obtain 23.5 g of a mixture of product and 3-bromopropionic acid.

Step B: Preparation of 5,6-Dihydro-4H-4-oxo-furano[2,3-b]thiopyran 5 g of the mixture from Step A was dissolved in 300 mL methylene chloride and cooled to 0° C. DMF (4 mL) was then added followed by oxalyl chloride (5.07 mL, 0.058 mol) slowly with stirring. After three hours, the reaction was cooled to −78° C. and $SnCl_4$ was added (6.8 mL, 0.058 mol) and the reaction warmed slowly to 0° over two hours. The reaction was poured into ∼1L $H_2O$ and the phases separated. The aqueous phase was extracted with $CH_2Cl_2$ and the combined organics were dried over $MgSO_4$, filtered and concentrated. Chromatography of the residue on silica gel eluting with 3:1 hexanes/ethyl acetate gave 720 mg (16%) of product as a viscous pale yellow oil. $^1$HNMR $CDCl_3$ δ7.37 (d,J=1.2 Hz,1H) 6.8 (m,1H) 3.35 (appt,J=5.5 Hz,2H) 2.78 (appt,J=5.5 Hz,2H).

Employing the procedures substantially as described in Example 8, Steps A and B, the following compound was prepared:

5,6-Dihydro-4H-6-methyl-4-oxo-furano[2,3-b]thiopyran (10% yield) $^1$HNMR $CDCl_3$ δ 7.35 (m,1H) 6.77 (m,1H) 3.9–3.7 (m,1H) 2.85–2.55 (m,2H) 1.5 (d,J=6 Hz,3H)

Step C: Preparation of 5,6-Dihydro-4H-4-oxo-furano-[2,3-b]thiopyran-2-sulfonamide.

The title compound was prepared in a manner analogous to Example 1, Step E.

MP=243°–245° C. 2.2 g 59% yield. $^1$HNMR $d_6$ DMSO δ7.92 (S,2H) 7.12(S,H) 3.55 (appt, J=5 Hz,2H) 2.75 (appt,J=5 Hz,2H).

Elemental analysis for $C_7H_7NO_4S_2$.

|  | C | H | N |
|---|---|---|---|
| Calculated: | 36.04 | 3.02 | 6.00 |
| Found: | 35.76 | 2.82 | 5.87 |

Similarly prepared was 5,6-Dihydro-4H-6-methyl-furano[2,3-b]thiopyran-4-one 2.31 g (35% yield). $^1$HNMR $d_6$ DMSO δ 7.92 (S,2H) 7.16 (S,1H) 4.2–4 (m,1H) 2.9–2.6 (m,2H) 1.45 (d,J=6 Hz,3H)

Step D: Preparation of 5,6-Dihydro-4H-4-oxo-furano-[2,3-b]thiopyran-7,7-dioxide-2-sulfonamide The title compound was prepared in a manner exactly analogous to that described in Example 5 to give 2.09 g; 75% yield, MP=217°–219° C. $^1$HNMR $d_6$ DMSO δ8.32 (S,2H) 7.30 (S,1H) 4.25 (appt,J=6 Hz,2H) 3.20 (appt,J=6 Hz,2H).

Elemental analysis calculated for $C_7H_7NO_6S_2$.

|  | C | H | N |
|---|---|---|---|
| Calculated: | 31.64 | 2.66 | 5.28 |
| Found: | 31.45 | 2.64 | 5.12 |

Step E: Preparation of 5,6-Dihydro-4H-4-isobutylamino[2,3-b]thiopyran-7,7-dioxide-2-sulfonamide Prepared in a manner analogous to that described in Example 6 from the corresponding 4-oxo-compound. It was crystallized from acetonitrile as the maleate salt. 74 mg, MP=164°–167° C. $^1$HNMR $d_6$ DMSO 8.35 (S,2H) 7.4 (S,2H) 4.5 (brs,1H) 3.95–3.7 (m,2H) 3.5–3.1 (brm,1H) 2.9–2.5 (m,4H) 1.9 (m,1H) 0.95 (m,brs).

Elemental analysis for $C_{11}H_{18}O_5N_2 \cdot C_4H_4O_4$.

|  | C | H | N |
|---|---|---|---|
| Calculated: | 41.09 | 5.06 | 6.39 |
| Found: | 41.47 | 5.77 | 6.34 |

EXAMPLE 9

5,6-Dihydro-4H-4-ethylamino-6-methylfurano[2,3-b]-thiopyran-2-sulfonamide-7,7 dioxide hydrochloride A solution of 470 mg (1.9 mmol) of 5,6-dihydro-4H-4-oxo-6-methylfurano[2,3-b]thiopyran in 50 ml ethanol at room temperature was treated with 180 mg (4.76 mmol) of $NaBH_4$ at room temperature for two hours. After working up as described in Example 2 a quantitative yield of the alcohol was obtained. This was dissolved in acetonitrile (50 mL) and cooled to −10° C. and treated with 103 mL (leq) of concentrated sulfuric acid. The reaction was stirred for 1.5 hours and then poured into water and extracted with ethyl acetate. The combined organics were dried over $MgSO_4$, filtered and concentrated in vacuo to give 508 mg (91%) of the crude product which was characterized as a mixture of cis and trans isomers by NMR. The mixture was not separated at this point but dissolved in 75 mL methanol and treated with 2.54 g, 4.15 mmol) of OXONE ® at room temperture for three days. After an aqueous workup as described in Example 4 and ethyl acetate extraction, the organic layers were dried over MgSO₄, filtered and concentrated in vacuo to give 320 mg of a colorless glass (60%). This material was also a mixture of cis and trans isomers and was carried on to the next step.

The amide sulfone was dissolved in 50 mL THF and treated with excess borane.DMS complex. The reaction was heated to reflux for four hours. The reaction was then treated with 5 mL 6N HCl and refluxed for 45 minutes. The reaction was cooled and concentrated to dryness in vacuo. The residue was dissolved in 1N HCl and extracted with ethyl acetate. The aqueous phase was then basified to pH9 and extracted repeatedly with ethyl acetate. The base extractions were combined, dried over MgSO₄, filtered and concentrated at reduced pressure. Chromatography of the residue on silica gel eluting with 10% methanol/chloroform gave 80 mg of the trans isomer which was crystallized as its hydrochloride salt from methanol/isopropanol to give 51 mg, MP=280° C.

¹HNMR d₆ DMSO δ 9.6 (brs,1H) 8.3 (S,2H) 7.58 (S,1H) 4.61–4.53 (m,1H) 4.4–4.2 (m,1H) 3.45–3.3 (m,1H) 3.3–3.1 (m,1H) 3.1–2.95 (m,1H) 2.75–2.5 (m,2H) 1.37 (d,J=6.8 Hz,3H) 1.27 (t,J=7.0 Hz,3H).

| Elemental analysis for $C_{10}H_{16}N_2O_5S_2 \cdot HCl \cdot 0.2\ C_3H_8O$. | | |
| --- | --- | --- |
| C | H | N |
| Calculated: 35.67 | 5.25 | 7.85 |
| Found: 35.85 | 5.02 | 7.85 |

EXAMPLE 10

Step A: Preparation of 2-(2-furanothio)succinic acid

A stirring solution of maleic acid (6.38 g, 0.055 mol) in tetrahydrofuran (50 ml) under a nitrogen atmosphere was treated with 2-mercaptofuran (5.5 g 0.055 mol) and triethylamine (14.2 g, 0.14 mol). The mixture was heated to reflux for 16–18 hrs overnight. The solvent was removed in vacuo and the residue was poured into 3N HCl (200 ml).

The product was then extracted into ethyl acetate. The ethyl acetate solution was washed with brine then dried over MgSO4, filtered, and concentrated in vacuo.

Step B: Preparation of 5,6-Dihydro-4-oxo-4H-furano[2,3-b]thiopyran-6-carboxylic acid To a stirred suspension of 2-(2-furanothio) succinic acid (75.5 g, 0.325 mol) in methylene chloride (500 ml) under a nitrogen atmosphere was added dimethylformamide (3 ml) followed by dropwise addition of oxalyl chloride (70.7 ml, 0.81 mol) over ½ hr. The mixture was stirred at room temperature for 2½ hrs and the resulting solution was concentrated in vacuo. The residual material was dissolved in methylene chloride (400 ml) and cooled to −70° C. and trifluoromethyl sulfonic acid (50 g, 033 mol) was added dropwise over 5 minutes. After 15 minutes at −78° C. the cooling bath was removed and the reaction was allowed to warm slowly to room temperature. The mixture was stirred at room temperature for 5 hrs. and poured into ice water. The product was extracted into ethyl acetate. The ethyl acetate solution was washed with 10×150 ml of 0.25N KOH. The aqueous extracts were acidified and the solid that separated was collected by filtration.

Step C: Preparation of N,N-Dimethyl-4-oxo-4H-furano[2,3-b]thiopyran-6-carboxamide To a stirred solution of 4-oxo-4H-furano[2,3-b]thiopyran-6-carboxylic acid (9.9 g, 0.05 mol) in tetrahydrofuran (50 ml) was added carbonyldimidazole (8.9 g, 0.055 mol). The mixture was stirred at ambient temperature for ¾ hr. Anhydrous dimethylamine was bubbled into the reaction mixture at 0° C. The reaction was stirred at 0° C. for ¾ hr. and the solvents were evaporated in vacuo. The residue was treated with H₂O (150 ml) and the solid that separated was collected and dried in vacuo.

Step D: Preparation of 5,6-Dihydro-6-dimethylaminomethyl-4H-furano[2,3-b]thiopyran To a stirring, refluxing solution of N,N-dimethyl-4-oxo-5,6-dihydro-4H-furano[2,3-b]thiopyran-6-carboxamide (7.1 g, 0.0314 mol) in tetrahydrofuran (150 ml) was added dropwise borane-dimethyl sulfide complex (9.4 ml, 0.014 mol). The reaction was then stirred at reflux for 3 hr. when 6NHCl (25 ml) was added slowly and the reaction was heated at reflux for a further ½ hr. Most of the tetrahydrofuran was removed in vacuo and the residue was diluted with 6N HCl (50 ml) and heated again for ½ hr. The reaction was cooled to room temperature and water (100 ml) was added. The reaction was extracted once with ether (50 ml) and then basified with 10N NaOH (75 ml). The product was extracted with ethyl acetate (4×50 ml portions). The ethyl acetate solution was dried over anhydrous sodium sulfate, filtered and concentrated in vacuo to give the product.

Step E: Preparation of 5,6-Dihydro-6-dimethylaminomethyl-4H-furano[2,3-b]thiopyran-2-sulfonamide n-Butyl lithium (9.4 ml, 0.015 mol of a 1.6M solution in hexane) was added dropwise over 15 minutes to a stirred solution of 5,6-Dihydro-6-dimethylamino-methyl-4H-furano[2,3-b]thiopyran (2.95 g, 0.0.15 mol) in tetrahydrofuran (25 ml) at −18° C. After ½ hr. at −78° C., anhydrous SO₂ was bubbled over the surface of the reaction until a neutral pH was achieved. The reaction was stirred at −78° C. for another 1 hr. The reaction was allowed to warm slowly to ambient temperature and the solvents were removed in vacuo. The residue was dissolved in 50 ml of H₂O and treated with sodium acetate (1.8 g 0.022 mol) and hydroxylamine-o-sulfonic acid (2.26 g, 0.02 mol). The reaction was stirred at room temperature for 18 hr. Excess saturated sodium bicarbonate was added and the mixture was extracted with ethyl acetate (3×50 ml). The ethyl acetate layers were combined and extracted with 1M KOH (2×30 ml). The aqueous phase was acidified with 6N HCl and extracted with ethyl acetate and dried over anhydrous magnesium sulfate. The crude material was purified by chromatography on silica gel, eluting with 10% methanol in chloroform.

Step F: Preparation of 5,6-Dihydro-6-dimethylaminomethyl-4H-furano[2,3-b]thiopyran-2-sulfonamide-7,7-dioxide and 5,6-Dihydro-6-methylene-4-H-furano[2,3-b]thiopyran-2-sulfonamide-7,7-dioxide 5,6-Dihydro-6-dimethylaminomethyl-4H-furano-[2,3-b]thiopyran-2-sulfonamide (1.37 g, 0.005 mol) was dissolved in 10 ml of ethanol and 5 ml of water and treated with OXONE ® (4.6 g, 0.0075 mol). The reaction was stirred at room temperature for 5 hrs. and then neutralized carefully by adding solid sodium bicarbonate. The mixture was diluted with $H_2O$ (20 ml) and ethyl acetate (25 ml) and filtered. The filtrate was concentrated in vacuo and the residue was chromatographed on silica gel using 10% methanol in chloroform to give approximately equal amounts of the two products.

Step G: Preparation of 5,6-Dihydro-6-(2-methylpropylaminomethyl)-4H-furano[2,3-b]thiopyran-2-sulfonamide-7,7-dioxide 5,6-Dihydro-6-methylene-4H-furano[2,3-b]thiopyran-2-sulfonamide-7,7-dioxide (0.55 g, 0.0021 mol) was dissolved in methanol (3 ml) and treated with isobutylamine (0.29 g, 0.004 mol). The solution was stirred at room temperature for 18 hrs. and the solvents were removed in vacuo. The residue was chromatographed on silica gel using 5% methanol in chloroform, to give the pure product. Following the procedure substantially as described in the previous example, but using the amines depicted below, there are produced the 6-substituted aminomethyl compounds also depicted below:

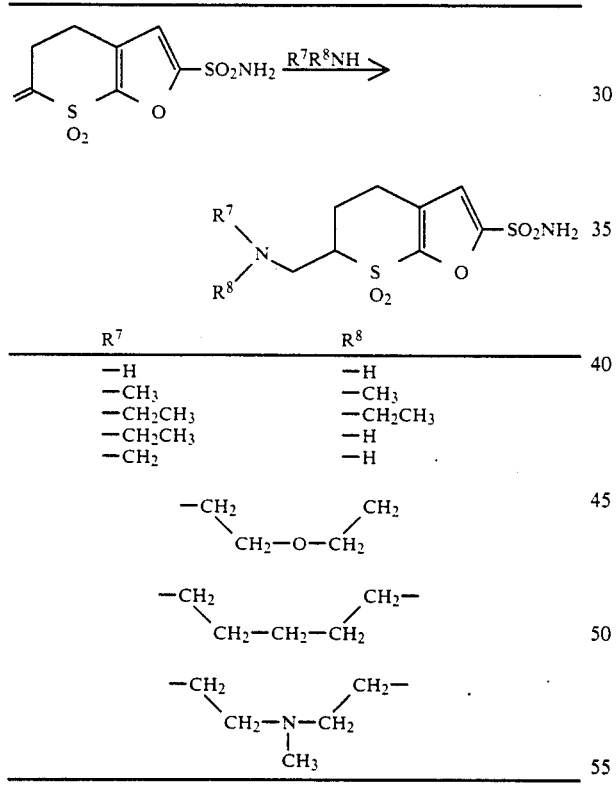

| $R^7$ | $R^8$ |
|---|---|
| —H | —H |
| —CH$_3$ | —CH$_3$ |
| —CH$_2$CH$_3$ | —CH$_2$CH$_3$ |
| —CH$_2$CH$_3$ | —H |
| —CH$_2$ | —H |
| —CH$_2$\CH$_2$—O—CH$_2$/CH$_2$ | |
| —CH$_2$\CH$_2$—CH$_2$—CH$_2$/CH$_2$— | |
| —CH$_2$\CH$_2$—N(CH$_3$)—CH$_2$/CH$_2$— | |

| 5,5-dimethyl-4,5-dihydro-4-oxofurano[2,3b]-thiophene-2-sulfonamide. | 1 mg | 15 mg |
|---|---|---|
| Monobasic sodium phosphate 2H$_2$O | 9.38 mg | 6.10 mg |
| Dibasic sodium phosphate .12H$_2$O | 28.48 mg | 16.80 mg |
| Benzalkonium chloride | 0.10 mg | 0.10 mg |
| Water for injection q.s. and. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 12

| 5,5-dimethyl-4,5-dihydro-4-hydroxyfurano[2,3-b]-thiophene-2-sulfonamide | 5 mg |
|---|---|
| petrolatum q.s. and. | 1 gram |

The compound and the petrolatum are aseptically combined.

EXAMPLE 13

| 5,6-Dihydro-5,5Odimethyl-4-ethylamino-4H-furano[2,3b] thiopyran-2-sulfonamide | 1 mg |
|---|---|
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R. H. at 30° C.) for two to four days. After removal from the humidity cabinet, the vials are stoppered and then capped. The vials containing the hydrate are then autocalved at 250° F. for ½ hour.

What is claimed is:
1. A compound of structural formula:

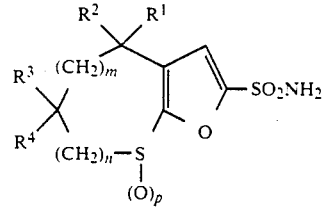

the individual diastereomers, the individual enantiomers or mixtures thereof, or an ophthalmologically acceptable salt thereof wherein:
$R^1$ is
1) hydrogen,
2) —NR$^5$R$^6$, wherein $R^5$ and $R^6$ independently are:
  a) hydrogen, or
  b) C$_{1-6}$alkyl;
$R^2$ is hydrogen; or
$R^1$ and $R^2$ taken together represent =O;
$R^3$ is
1) hydrogen,
2) C$_{1-6}$alkyl, either unsubstituted or substituted with
  a) hydroxy,
  b) C$_{1-3}$alkoxy,
  c) C$_{1-3}$alkoxy-C$_{2-3}$alkoxy,
  d) hydroxy-C$_{2-3}$alkoxy, or
  e) —NR$^7$R$^8$ wherein R$^7$ and R$^8$ independently are:
    i) hydrogen, or
    ii) C$_{1-6}$alkyl,
3) C$_{2-6}$alkenyl, or
4) C$_{2-6}$alkynyl;

$R^4$ is hydrogen or $C_{1-6}$alkyl;

m and n are independently 0, or 1 with the proviso that m+n must be equal to 1; and p is 0 or 2.

2. The compound of claim 1, wherein $R^1$ is $-NR^5R^6$.

3. The compound of claim 2 wherein one of $R^5$ and $R^6$ is hydrogen and the other is $C_{1-6}$alkyl.

4. The compound of claim 2 wherein p is 2.

5. The compound of claim 3 wherein P is 2.

6. An ophthalmological formulation for the treatment of ocular hypertension comprising an ophthalmologically acceptable carrier and an effective ocular antihypertensive amount of a compound of claim 1.

7. A method of lowering elevated intraocular pressure comprising the administration to a patient in need of such treatment of an effective intraocular pressure lowering amount of the compound of claim 1.

* * * * *